United States Patent

Gilman

Patent Number: 5,086,764
Date of Patent: Feb. 11, 1992

[54] ABSORBENT DRESSING

[76] Inventor: Thomas Gilman, 6 Jacob Dr., Mansfield, Mass. 02048

[21] Appl. No.: 337,240

[22] Filed: Apr. 13, 1989

[51] Int. Cl.$^5$ .................. A61F 13/00; A61F 15/00
[52] U.S. Cl. .................. 602/42; 128/888; 602/54
[58] Field of Search .............. 128/155, 156, 165, 846, 128/857, 877, 880, 881, 858, 889, 888, 893, 894, 887; 604/366, 368, 358, 370, 380, 382, 383, 895, 897

[56] References Cited

U.S. PATENT DOCUMENTS

| 3,121,021 | 2/1964 | Copeland | 128/156 |
| 3,658,065 | 4/1972 | Hirsch | 128/156 X |
| 3,888,247 | 6/1975 | Stenvall | 128/155 |
| 4,399,816 | 8/1983 | Spangler | 128/888 |
| 4,427,737 | 1/1984 | Cilento et al. | 128/156 |
| 4,450,845 | 5/1984 | Engel | 128/846 X |
| 4,649,909 | 3/1987 | Thompson | 128/155 |
| 4,669,458 | 6/1987 | Abraham et al. | 128/846 |

Primary Examiner—Alan Cannon
Assistant Examiner—Paul Prebilic

[57] ABSTRACT

A dressing for a wound of a patient having, an absorbent fabric, a base sheet for placement on the skin of the patient surrounding the wound, with the base sheet having an opening extending therethrough located over the wound and being sufficiently large to receive the absorbent fabric into the wound, with the base sheet having adhesive on a front surface thereof for securement of the base sheet to the skin surrounding the wound. The dressing has a cover sheet resistant to the passage of bacteria, with the cover sheet having dimensions larger than the opening. The cover sheet is secured over the base sheet in a position to cover the opening.

5 Claims, 1 Drawing Sheet

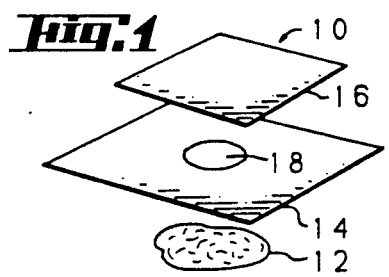
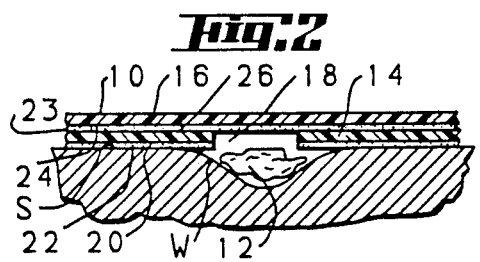
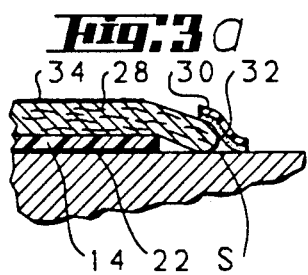
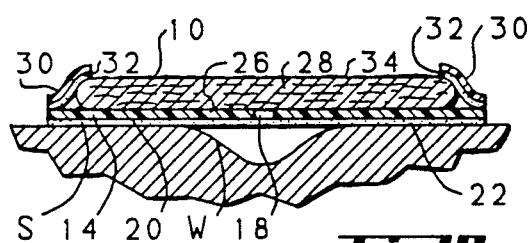
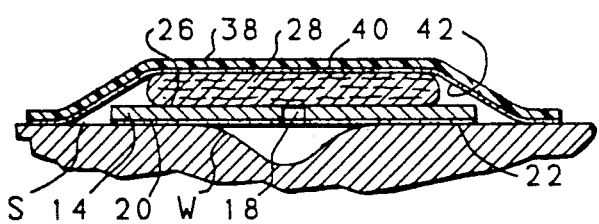
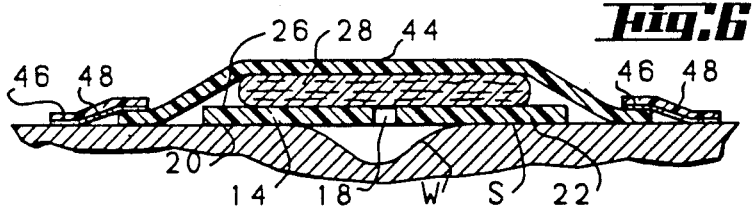
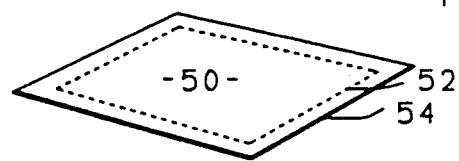
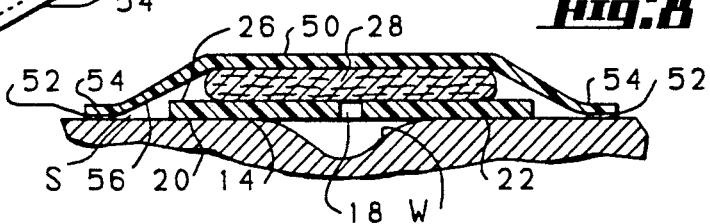

ABSORBENT DRESSING

BACKGROUND OF THE INVENTION

In the case of a draining wound, it is often necessary to change the absorbent medium in the wound on a twelve hour or more frequent basis, since the absorbent becomes saturated with fluid. In the past, where the covering media comprises a transparent dressing, such as Polyskin, a trademark of The Kendall Company, Boston, Mass., has certain advantages, such as serving as a bacterial barrier, and a barrier to fluid. These advantages apply both to the care of protecting the wound from outside contaminants and to protecting the patient's healthy skin from the wound exudate. In addition, such a dressing helps maintain a moist environment where desiccation can be detrimental.

However, there is a disadvantage to changing this type of dressing, which has adhesive on a first surface thereof, twice a day, since the skin to which it is attached becomes "tape stripped" by repeated removal of the adhesive dressing. This procedure irritates the skin, and affects its natural barrier. Also, such a dressing does not have the ability to handle wound fluid, since the fluid builds up in a pressure bubble beneath the dressing, which tends to undermine the adhesive seal to the skin, and can lead to contamination of the wound by skin organisms.

SUMMARY OF THE INVENTION

A principal feature of the present invention is the provision of an improved dressing for a wound for a patient of simplified construction.

In one form, the dressing comprises an absorbent fabric, a base sheet comprising an elastomer film for placement on the skin of the patient surrounding the wound, with the base sheet having an opening extending therethrough located over the wound and being sufficiently large to receive the absorbent fabric into the wound, with the base sheet having an adhesive on a front surface thereof for securement of the base sheet to the skin surrounding the wound. The dressing has a cover sheet comprising an elastomer film resistant to the passage of bacteria, with the cover sheet having dimensions larger than the opening, and means for releasably securing the cover sheet over the base sheet in a position to cover the opening.

A feature of the present invention is that the cover sheet may be readily removed from the base sheet in order to replace the dressing in the wound without removal of the base sheet. Thus, the dressing of the present invention eliminates the "tape stripping" associated with the prior dressings.

Another feature of the present invention is that the dressing provides a bacterial barrier to the wound.

Yet another feature of the invention is that the dressing has the capability of handling the wound fluid, and minimizes the possibility of undermining the adhesive of the base sheet surrounding the skin, thus minimizing the possibility of contamination of the wound by skin organisms.

A further feature of the invention is that the absorbent fabric may be replaced in the wound in a simplified manner.

Another feature of the invention is that in a different form the absorbent fabric may be releasably secured over the base sheet, and may be replaced in a simplified manner without removal of the base sheet.

Further features will become more fully apparent in the following description of the embodiments of this invention and from the appended claims.

DESCRIPTION OF THE DRAWINGS

In the drawings:

FIG. 1 is an exploded perspective view of a dressing according to the present invention;

FIG. 2 is a fragmentary sectional view of the dressing of FIG. 1 as positioned over a wound of a patient;

FIG. 3 is a sectional view of another embodiment of a dressing of the present invention;

FIG. 3a is a fragmentary sectional view of another embodiment of the dressing of FIG. 3;

FIG. 4 is a sectional view of an absorbent layer for the dressing of FIG. 3;

FIG. 5 is a sectional view of another embodiment of a dressing of the present invention;

FIG. 6 is a sectional view of another embodiment of a dressing of the present invention;

FIG. 7 is a perspective view of a back sheet for a dressing of FIG. 8; and

FIG. 8 is a sectional view of another embodiment of a dressing of the present invention.

DESCRIPTION OF THE PREFERRED EMBODIMENTS

Referring now to FIGS. 1 and 2, there is shown a dressing generally designated 10 for a wound W of a patient, with the skin S of the patient surrounding the wound W. The dressing 10 has an absorbent fabric 12, such as a gauze sponge, a base sheet 14, and a cover sheet 16. As shown, the base sheet 14 has an opening 18 extending therethrough and located over the wound W when the base sheet 14 is placed on the skin S of the patient surrounding the wound W. The base sheet 14 has a pressure-sensitive adhesive 22, such as an acrylic adhesive or hydrocolloid adhesive, on a front surface 20 of the base sheet 14 for securing the base sheet 14 to the skin S of the patient surrounding the wound W with the opening 18 being located over the wound W. As shown, the opening 18 of the base sheet 14 is sufficiently large to receive the absorbent fabric 12 for placement in the wound W, and, in a preferred form, the opening 18 of the base sheet 14 is smaller in dimensions than the size of the wound W, such that the base sheet 14 can be sealed up to the edge of the wound W.

The cover sheet 16 is resistant to the passage of bacteria, and the cover sheet 16 has dimensions larger than the opening 18 of the base sheet 14. As shown, the cover sheet 16 has a pressure-sensitive adhesive 23, such as an acrylic adhesive, on a front surface 24 of the cover sheet 16 for releasably securing the cover sheet 16 to a back surface 26 of the base sheet 14 at a location such that the cover sheet 16 extends across and covers the opening 18 of the base sheet 14. The base sheet 14 and cover sheet 16 may comprise suitable elastomer films such as Polyskin, a trademark of the Kendall Company, Boston, Mass., which is moisture vapor permeable elastomer film, such as a polyurethane film. Alternatively, the cover sheet 16 may comprise a film constructed from HYTREL, a trademark of E. i. DuPont DeNemours, Wilmington, Del., which comprises polyester polyether block polymer.

In use, the base sheet 14 is secured to the skin S of the patient surrounding the wound W, with the opening 18 centrally located over the wound W. The absorbent fabric 12 is placed through the opening 18 into the wound W, and the cover sheet 16 is secured over the base sheet 14 in order to close the opening 18 and provide a bacterial barrier to the wound W. When the time is appropriate to change the absorbent fabric 12, the cover sheet 16 is removed from the base sheet 14 without removal of the base sheet 14 from the skin S of the patient. The saturated absorbent fabric 12 is removed from the wound W, and a new absorbent fabric 12 is placed through the opening 18 of the base sheet 14 into the wound W. In this manner, the absorbent fabric 12 may be changed without requiring the base sheet 14 to be removed from the skin S of the patient in order to eliminate "tape stripping" caused by previous removal of such a sheet with adhesive which contacts the skin S of the patient. Thus, the dressing of the present invention eliminates irritation to the skin S of the patient, while providing a bacterial barrier to the wound W. The dressing 10 of the present invention also has the ability to handle wound fluid by the absorbent fabric 12, which eliminates the tendency to undermine the adhesive seal to the skin S of the patient surrounding the wound W, which could otherwise lead to contamination of the wound by skin organisms.

EXAMPLE

A two inch by four inch base sheet was used as the bottom layer with a 15/16 inch circular hole being die cut through the base sheet which is placed on the skin. A cover sheet was cut to dimensions of 1¾ inch by 1¾ inch size, and was placed over the base sheet opening. An excellent seal between the cover sheet and base sheet was observed, and the dressing was impervious to liquid water placed on top of the dressing.

The cover sheet was easily removed from the base sheet, without disrupting the base sheet placement, and another 1¾ by 1¾ inch cover sheet was placed over the base sheet, which was also easily removed.

Another embodiment of the present invention is illustrated in FIG. 3, in which like reference numerals designate like parts. In this embodiment, the base sheet 14 is constructed in a similar manner as the base sheet 14 disclosed in connection with FIGS. 1 and 2, with the exception that the opening 18 may be constructed of much smaller dimensions, in particular substantially smaller than the dimensions of the wound W. Also, the base sheet 14 and corresponding adhesive 22 may be constructed of the same material that is disclosed in connection with FIGS. 1 and 2. In this embodiment, the dressing 10 has an absorbent layer 28, such as a gauze sponge, located on the back surface 26 of the base sheet 14 in a position such that it covers the opening 18 of the base sheet 14. In this embodiment, the absorbent layer 28 has dimensions smaller that the base sheet 14, and the absorbent layer 28 may be releasably secured to the base sheet 14 by a plurality of tape strips 30 having a pressure-sensitive adhesive 32 on a front surface of the tape strips 30, such that the tape strips 30 are releasably secured between the absorbent layer 28 and the base sheet 14 in order to releasably secure the absorbent layer 28 in place on the base sheet 14. In one form, as shown in FIG. 3, the back surface 34 of the absorbent layer 28 has a hydrophobic coating, such as a fluorocarbon, such as Scotch Guard, a trademark of 3M, St. Paul, Minn., in order to provide a fluid barrier for the absorbent layer 28 and make the dressing 10 resistant to contamination. In an alternative form, as shown in FIG. 4, the absorbent layer 28 may have a suitable film 36, such as the materials disclosed in connection with the base sheet 14, laminated or otherwise secured to the back surface 34 of the absorbent layer 28, with the film 36 being resistant to passage of bacteria in order to provide a bacterial barrier for the absorbent layer 28.

In use, the base sheet 14 is secured to the skin S by its associated adhesive 22 with the opening 18 located over the wound W. Next, the absorbent layer 18 is placed over the back surface 26 of the base sheet 14, and is secured in place by the tape strips 30. In this configuration, the absorbent layer 28 is releasably secured in place on the base sheet 14, and the excess fluid from the wound W passes through the opening 18 of the base sheet 14 into the absorbent layer 28 in order to prevent undermining of the adhesive 22 associated with the base sheet 14 surrounding the wound W. The fluid resistant covering for the back surface 34 of the absorbent layer 28 provides a bacterial barrier for the wound W in order to exclude outside bacteria by ensuring there is not a fluid path between the external environment and the wound W. Also, when the absorbent layer 28 becomes saturated with fluid from the wound W, the tape strips 30 may be removed, and a new absorbent layer 28 may be placed over the base sheet 14, and secured in place by new tape strips 30, such that the absorbent layers 28 may be replaced in a simplified manner while leaving the base sheet 14 intact on the skin S of the patient in order to prevent "tape stripping" by the adhesive 22 associated with the base sheet 14.

Another embodiment of the present invention is illustrated in FIG. 3a, which like reference numerals designate like parts. In this embodiment, the dressing 10 is similar to the dressing disclosed in connection with FIG. 3, with the modification that the absorbent layer 28 has dimensions larger than the base sheet 14, and the outer margins of the absorbent layer 20 may be releasably secured to the skin S by the tape strips 30 in order to releasably secure the absorbent layers 28 in place over the base sheet 14. In other respects, the dressing of FIG. 3a operates in the same manner as the dressing disclosed in connection with FIG. 3. Of course, the absorbent layer 28 may have the bacteria resistant back portion previously disclosed in connection with FIG. 3.

Another embodiment of the present invention is illustrated in FIG. 5, in which like reference numerals designate like parts. In this embodiment, the base sheet 14 is substantially identical to the base sheet 14 disclosed in connection with FIG. 3, and is positioned on the patient's skin S with the opening 18 located over the wound W. In this embodiment, the dressing 10 has an absorbent layer 28, but it is not necessary to provide the absorbent layer with a fluid resistant back portion as previously described. Rather, the dressing 10 has a back sheet 38 comprising a film resistant to the passage of bacteria, such as the elastomer materials disclosed in connection with the base sheet 14. In this embodiment, the back sheet 38 has dimensions larger than the base sheet 14, and has a pressure-sensitive adhesive 40, such as an acrylic adhesive, on a front surface 42 of the back sheet 38, such that peripheral margins of the back sheet 38 may be releasably attached to the skin S of the patient. Thus, the back sheet 38 provides a bacteria barrier for the dressing 10 during use. As before, the base sheet 14 is initially secured to the skin S of the patient with the opening 18 located over the wound W. Next, the absorbent layer 28 is placed over the base sheet 14, and the back sheet 38 is secured over the absorbent layer 28, as previously described. In this configuration, excess fluid from the wound W pass through the opening 18 of the base sheet 14 into the absorbent layer 28 in order to prevent undermining of the adhesive 22 associated with the base sheet 14, and the saturated absorbent layers 28 may be readily changed by removing the back sheet 38 and replacing the back sheet 38 over a new absorbent layer 28. Once again, it is unnecessary to remove the base sheet 14 from the skin S of the patient during the change of absorbent layers 28 in order to prevent "tape stripping" as previously described.

Another embodiment of the present invention is illustrated in FIG. 6, in which like reference numerals designating like parts. In this embodiment, the base sheet 14 is constructed substantially identical to the base sheet 14 disclosed in connection with FIG. 3, and is secured in place on the skin S of the patient with the opening 18 of the base sheet 14 located over the wound W, as previously described. In this embodiment, the dressing 10 has an absorbent layer 28 similar to the absorbent layer 28 described in connection with FIG. 5 in which it is unnecessary to provide a bacteria resistant back portion of the absorbent layer 28. In this embodiment, the dressing 10 has a back sheet 44 comprising an elastomer film resistant to the passage of bacteria therethrough, such as the material disclosed in connection with the base sheet 14. As shown, the dimensions of the back sheet 44 are larger than the dimensions of the base sheet 14, and peripheral margins of the back sheet 44 are releasably secured to the patient's skin S by suitable tape strips 46 with adhesive 48 on a front surface thereof. As previously described, excess fluids from the wound W pass through the opening 18 of the base sheet 14 into the absorbent layer 28 in order to prevent undermining of the adhesive 22 associated with the base sheet 14 peripherally around the wound W. The back sheet 44 provides a bacterial barrier for the dressing 10 during use, and the back sheet 44 may be readily removed from the dressing 10 by removal of the tape strips 46 in order to replace a new absorbent layer 28 when the previous absorbent layer 28 has become saturated with fluid from the wound W. The back sheet 44 may be readily secured in place over the new absorbent layer 28 through use of new tape strips 46 which are releasably secure to the skin S of the patient. Once again, the absorbent layers 28 may be readily replaced in a simplified manner while leaving the base sheet 14 intact on the skin S of the patient in order to prevent "tape stripping" by the adhesive 22 associated with the base sheet 14.

Another embodiment of the present invention is illustrated in FIGS. 7 and 8, in which like reference numerals designate like parts. In this embodiment, the base sheet 14 is constructed in substantially the manner disclosed in connection with FIG. 3, and is secured in place on the skin S of the patient with the opening 18 of the base sheet 14 located over the wound W. The dressing 10 has an absorbent layer 28 substantially identical as described in connection with FIG. 5, and it is not necessary to provide a bacteria resistant back portion of the absorbent layer 28. In this embodiment, the dressing 10 has a back sheet 50 comprising an elastomer film which is resistant to passage of bacteria therethrough, such as the materials disclosed in connection with the base sheet 14. As shown, the back sheet 50 has dimensions larger than the base sheet 14, and the back sheet 50 has a layer 52 of pressure-sensitive adhesive extending peripherally around the outer margins 54 of the back sheet 50 on a front surface 56 of the back sheet 50. In a preferred form, the layer 52 of adhesive comprises a hydrocolloid adhesive such as Duodern, a trademark of E. R. Squibb and Sons, Inc., Princeton, N.J., or Confeel, a trademark of Colloplast A/S, Denmark. Such an adhesive provides a seal to the skin S of the patient which is extremely resistant to liquid undermining by external fluids. Such a hydrocolloidal adhesive comprises a rubber based pressure-sensitive adhesive which is blended with hydrocolloid (water swellable) particles. Thus, the peripheral layer 52 of hydrocolloid adhesive excludes external liquid from the wound W, and prevents this liquid such as incontinent discharge, from undermining the dressing from the outside. In other respects, the dressing of FIGS. 7 and 8 operates in a manner as previously described. The excess fluids from the wound W pass through the opening 18 of the base sheet 14 into the absorbent layer 28. When it is desired to replace a saturated absorbent layer 28, the back sheet 50 may be readily removed from the skin S of the patient, and a new absorbent layer 28 may be placed over the base sheet 14, after which the original or new back sheet 50 is positioned and releasably secured in place over the new absorbent layer 28. Thus, the absorbent layers 28 may be readily changed, and the base sheet 14 remains in place on the skin S of the patient in order to prevent "tape stripping" by the adhesive 22 associated with the base sheet 14, as previously described.

Alternatively, the dressing of FIGS. 7 and 8 may have an adhesive layer between the back sheet 50 and absorbent layer 28, such that the back 50 and absorbent layer 28 may be simultaneously removed and a new back sheet 50 and absorbent layer 28 secured in place by adhesive layer 52.

The foregoing detailed description is given for clearness of understanding only, and no unnecessary limitations should be understood therefrom, as modifications will be obvious to those skilled in the art.

What is claimed is:

1. A dressing for a wound of a patient, comprising:
a base sheet for placement on the skin of the patient surrounding the wound, said base sheet having an opening extending therethrough located over the wound, said base sheet having an adhesive on a front surface there of for securement of the base sheet to the skin surrounding the wound;
an absorbent layer separate from the base sheet and located on a back surface of the base sheet, said layer covering the opening to permit replacement of the absorbent layer without removal of the base sheet from the patient's skin, with said layer having dimensions larger than said opening, said absorbent layer having a back surface comprising a hydrophobic coating in order to provide a barrier for the absorbent layer and make the dressing resistant to contamination; and
means for securing the absorbent layer in place over the base sheet.

2. The dressing of claim 1 wherein the absorbent layer has dimensions smaller than the base sheet, and the securing means comprises at least one tape strip having an adhesive releasably securing the absorbent layer to the base sheet.

3. The dressing of claim 1 wherein the absorbent layer has a back surface resistant to the passage of bacteria therethrough.

4. The dressing of claim 1 wherein the adhesive of the base sheet comprises an acrylic pressure-sensitive adhesive.

5. The dressing of claim 1 wherein the adhesive of the base sheet comprises a hydrocolloid adhesive.

* * * * *